(12) United States Patent
McKay

(10) Patent No.: US 7,018,415 B1
(45) Date of Patent: Mar. 28, 2006

(54) EXPANDABLE SPINAL FUSION DEVICE AND METHODS OF PROMOTING SPINAL FUSION

(75) Inventor: William F. McKay, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 178 days.

(21) Appl. No.: 10/252,299

(22) Filed: Sep. 23, 2002

(51) Int. Cl.
*A61F 2/44* (2006.01)

(52) U.S. Cl. ................. 623/17.15; 623/17.16

(58) Field of Classification Search ............. 623/17.11, 623/17.13, 17.12, 17.15, 17.16, 17.14
See application file for complete search history.

(56) References Cited

U.S. PATENT DOCUMENTS

| | | | |
|---|---|---|---|
| 4,309,777 A | 1/1982 | Patil | |
| 4,553,273 A | 11/1985 | Wu | |
| 4,599,086 A | 7/1986 | Doty | |
| 4,636,217 A | 1/1987 | Ogilvie et al. | |
| 4,863,476 A | 9/1989 | Shepperd | |
| 5,397,364 A * | 3/1995 | Kozak et al. | 623/17.11 |
| 5,458,641 A * | 10/1995 | Ramirez Jimenez | 623/17.11 |
| 5,522,899 A | 6/1996 | Michelson | |
| 5,554,191 A * | 9/1996 | Lahille et al. | 623/17.11 |
| 5,653,763 A * | 8/1997 | Errico et al. | 623/17.11 |
| 5,665,122 A * | 9/1997 | Kambin | 623/17.16 |
| 5,865,848 A | 2/1999 | Baker | |
| 5,980,522 A | 11/1999 | Koros et al. | |
| 6,015,436 A | 1/2000 | Schonhoffer | |
| 6,019,793 A | 2/2000 | Perren et al. | |
| 6,045,579 A | 4/2000 | Hochshuler et al. | |
| 6,080,193 A * | 6/2000 | Hochshuler et al. | 623/17.16 |
| 6,102,950 A * | 8/2000 | Vaccaro | 623/17.16 |
| 6,146,420 A * | 11/2000 | McKay | 623/17.16 |
| 6,159,245 A * | 12/2000 | Meriwether et al. | 623/17.11 |
| 6,190,414 B1 | 2/2001 | Young et al. | |
| 6,375,683 B1 * | 4/2002 | Crozet et al. | 623/17.15 |
| 6,454,806 B1 * | 9/2002 | Cohen et al. | 623/17.15 |
| 6,719,796 B1 | 4/2004 | Cohen et al. | |
| 6,770,096 B1 | 8/2004 | Bolger et al. | |
| 2002/0010511 A1 * | 1/2002 | Michelson | 623/17.15 |
| 2002/0068977 A1 * | 6/2002 | Jackson | 623/17.15 |
| 2002/0128716 A1 | 9/2002 | Cohen et al. | |
| 2003/0163199 A1 | 8/2003 | Boehm et al. | |
| 2003/0187436 A1 | 10/2003 | Bolger et al. | |
| 2003/0187441 A1 | 10/2003 | Bolger et al. | |

FOREIGN PATENT DOCUMENTS

| | | |
|---|---|---|
| DE | 201 09 599 U1 | 8/2001 |
| DE | 101 13 689 C1 | 8/2002 |
| EP | 0 425 542 B1 | 1/1995 |
| EP | 0 950 389 A2 | 10/1999 |
| FR | 2 795 627 A1 | 1/2001 |
| WO | WO 92/14423 | 9/1992 |

(Continued)

Primary Examiner—David O. Reip
(74) Attorney, Agent, or Firm—Woodard, Emhardt, Moriarty, McNett & Henry LLP

(57) ABSTRACT

An intervertebral disc space implant includes spaced-apart bone engagement portions that define an intermediate chamber that holds bone growth inducing material into contact with adjacent vertebral bodies. The implant is expandable to establish and maintain desired intervertebral spacing during fusion. The implant includes a first member and a second member arranged to move relative to each other by action of an expansion member, the first member being engageable with the vertebral body below the disc space.

17 Claims, 8 Drawing Sheets

FOREIGN PATENT DOCUMENTS

| | | | |
|---|---|---|---|
| WO | WO 01/56513 A1 * | 8/2001 | .............. 623/17.11 |
| WO | WO 02/09626 A1 | 8/2001 | |
| WO | WO 01/72246 A1 | 10/2001 | |
| WO | WO/02/24121 A2 | 3/2002 | |
| WO | WO 02/045629 A1 | 6/2002 | |
| WO | WO 02/45629 A1 | 6/2002 | |

* cited by examiner

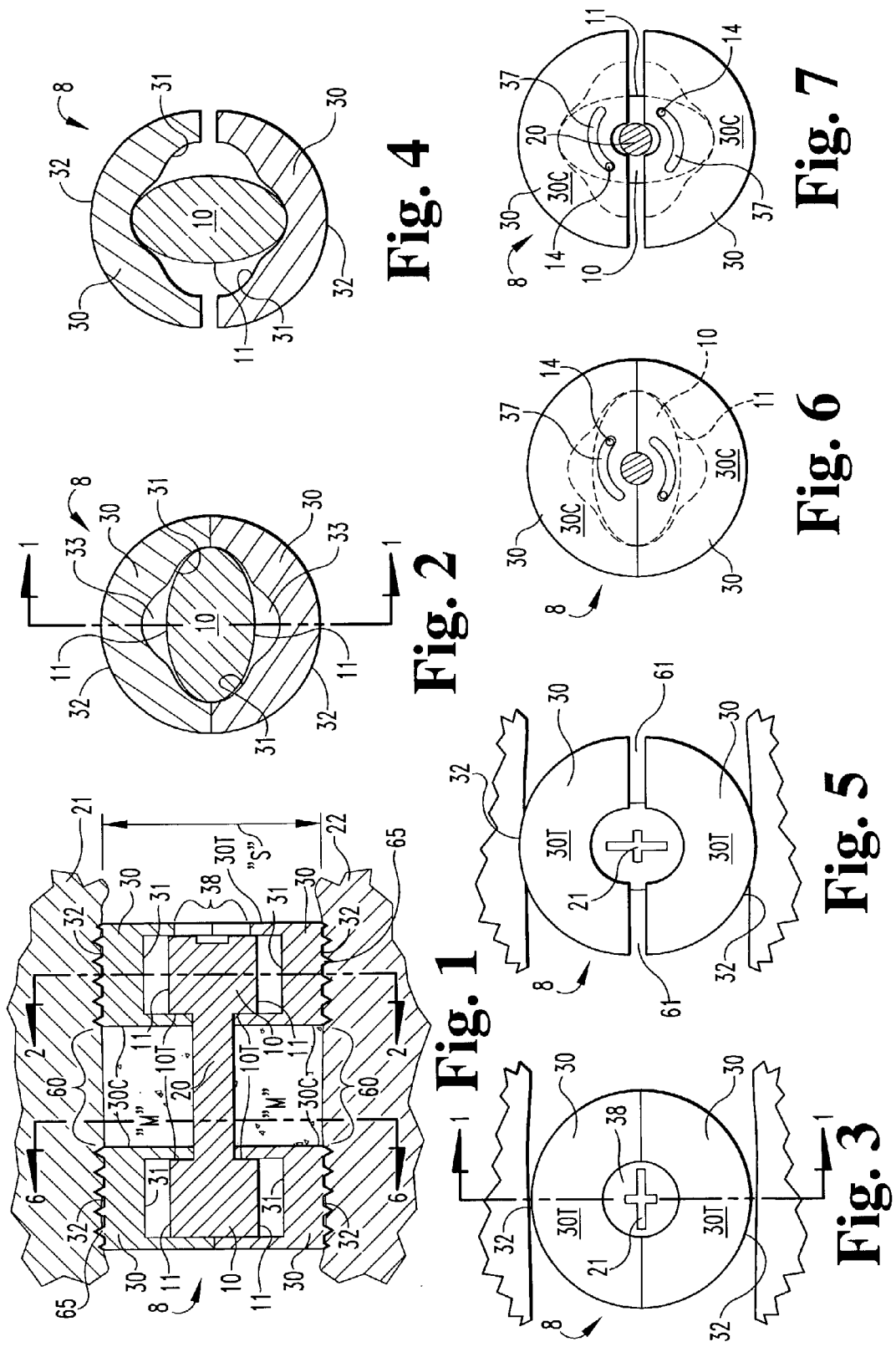

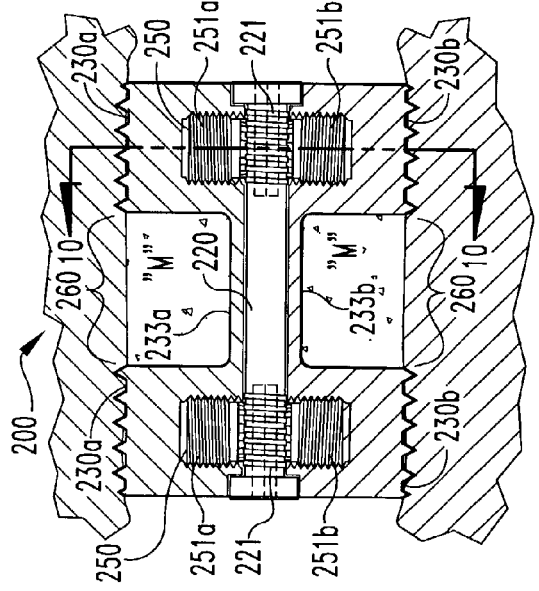
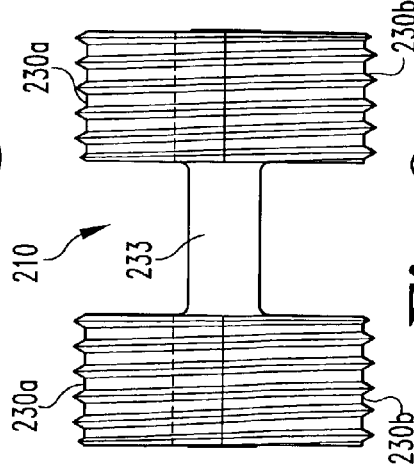
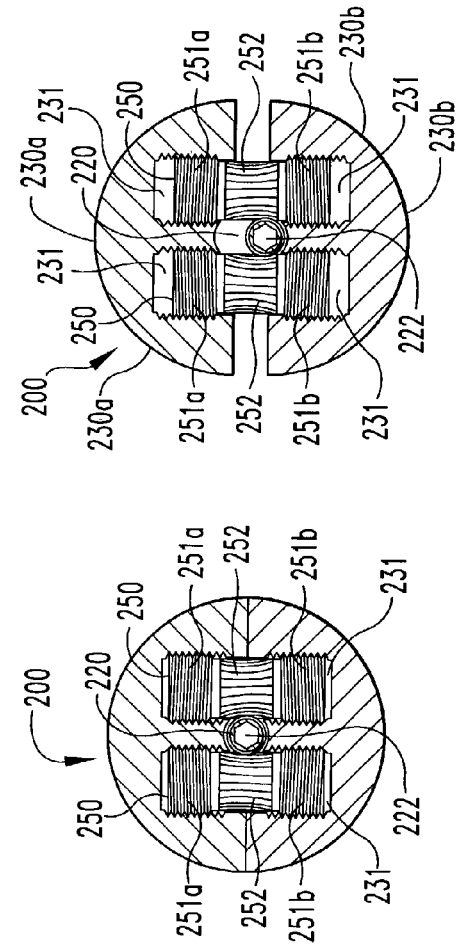
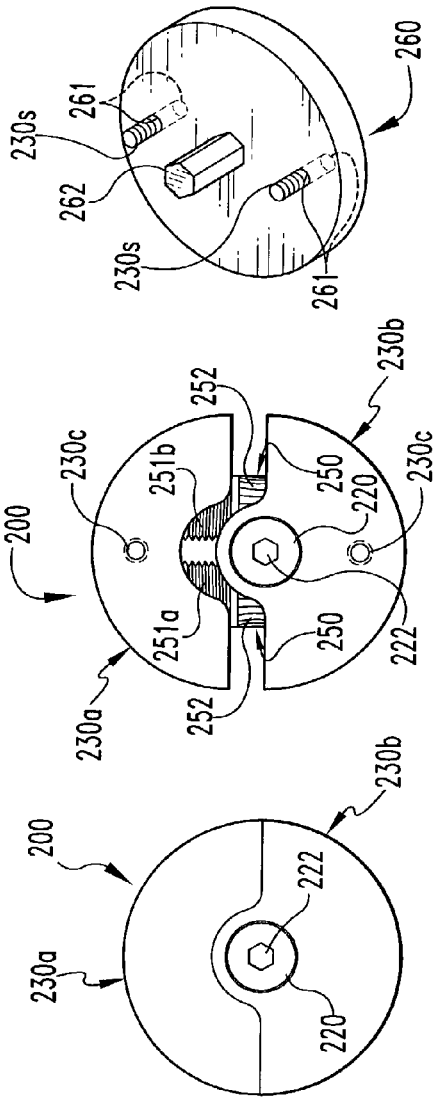

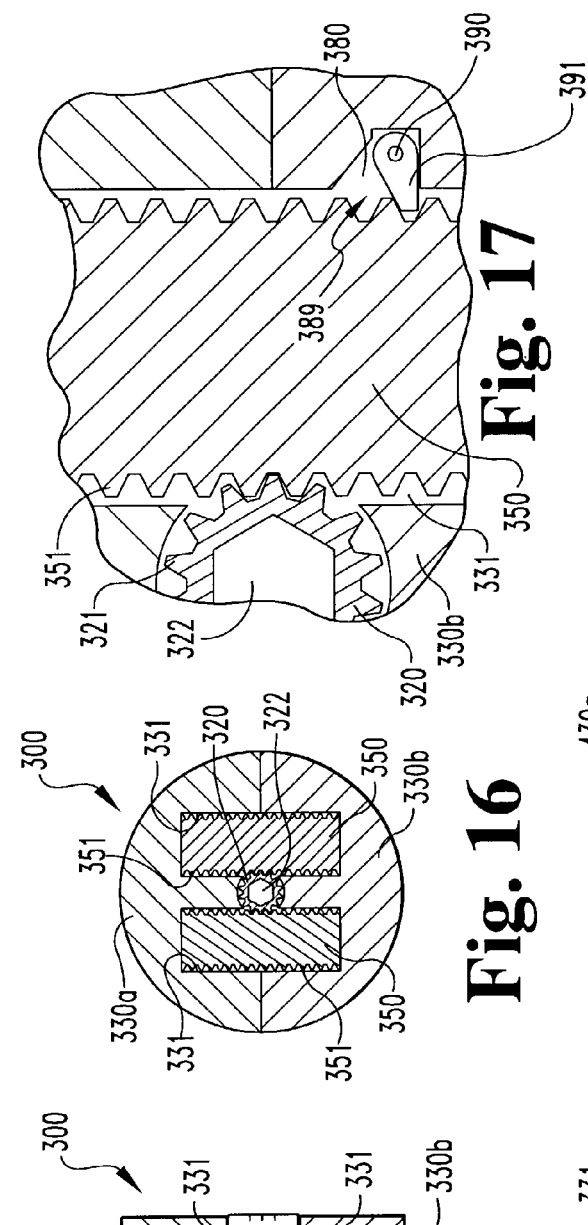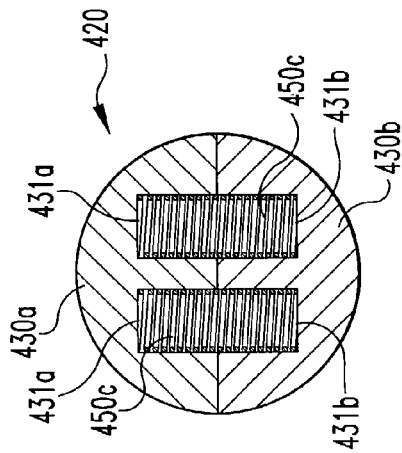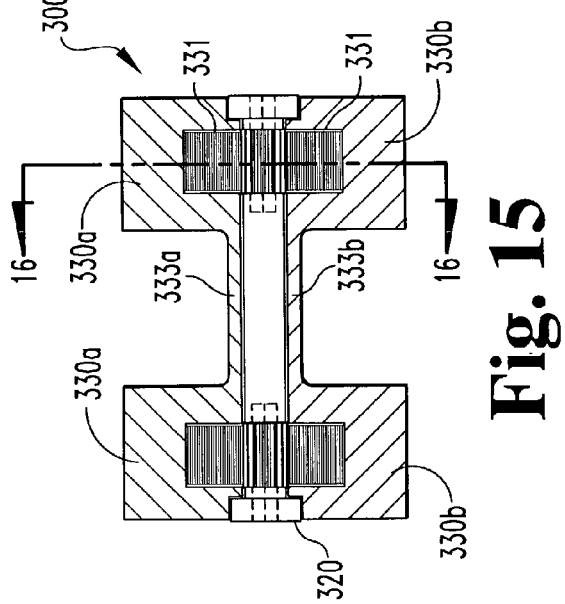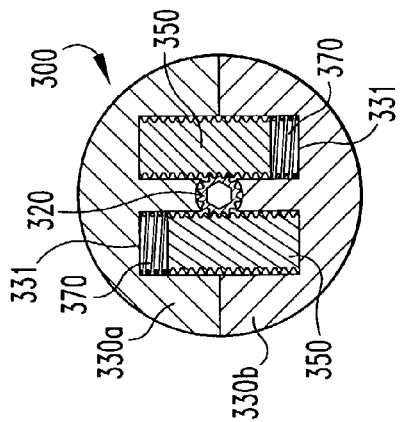

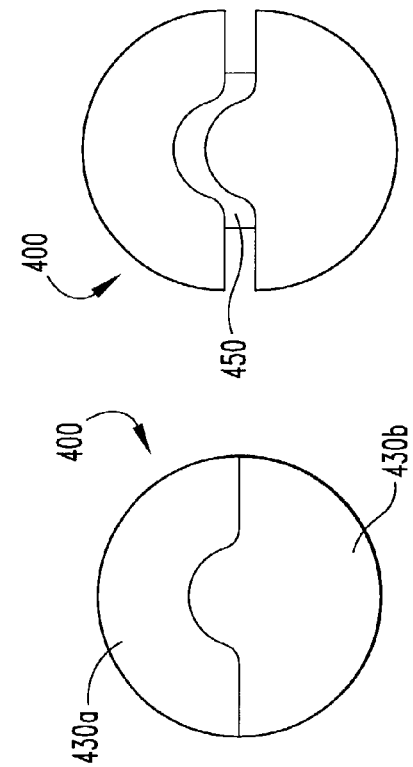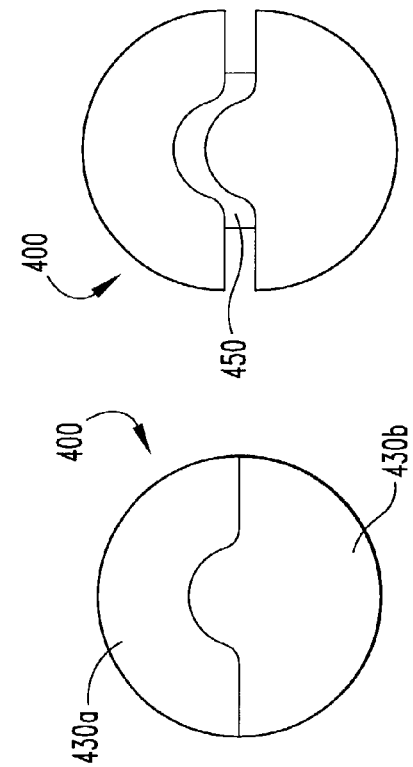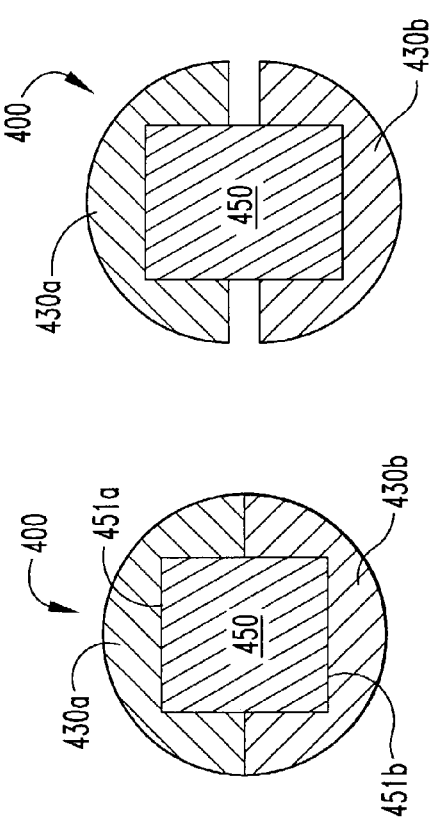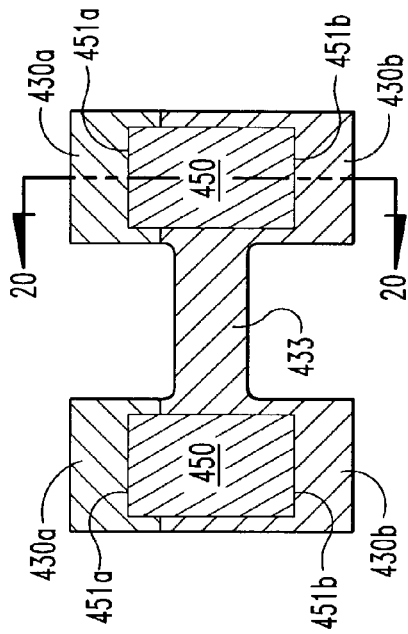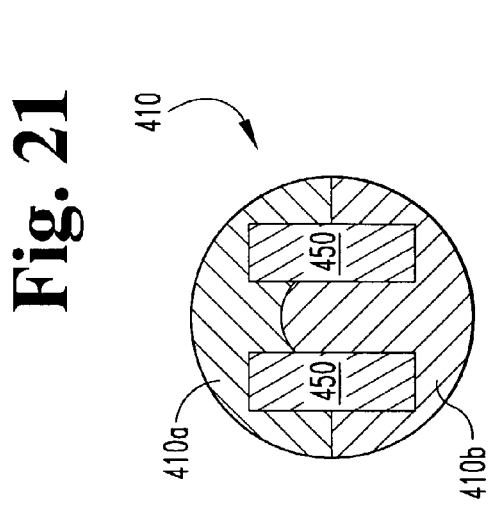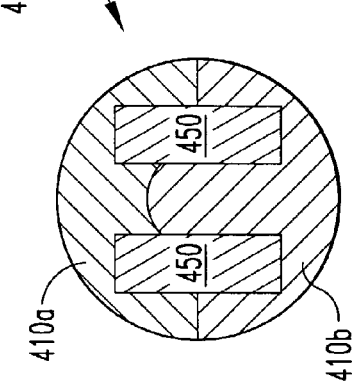

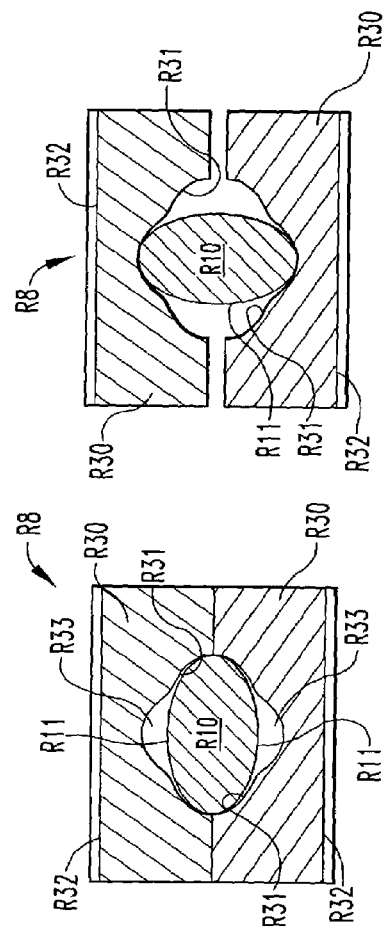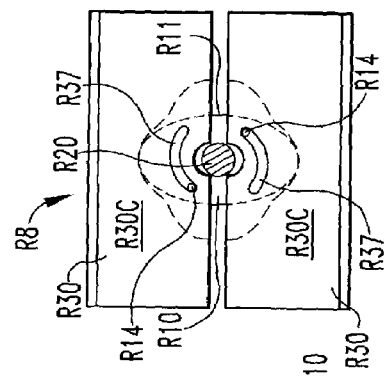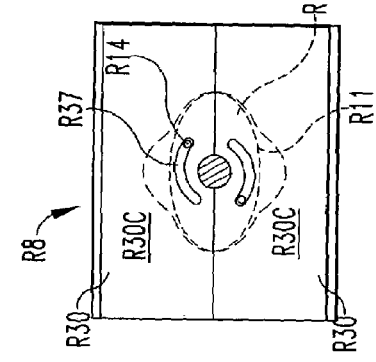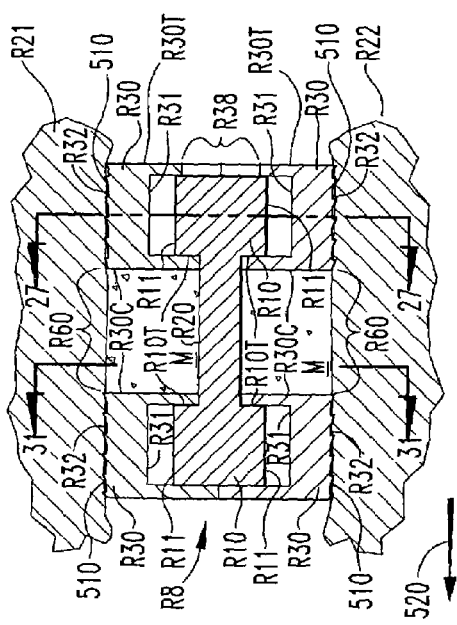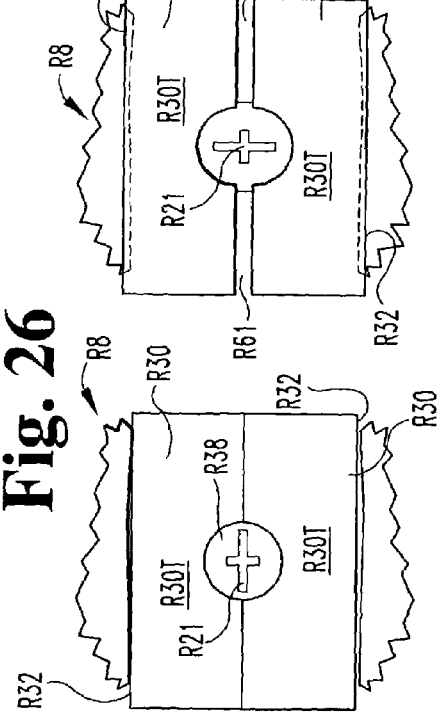

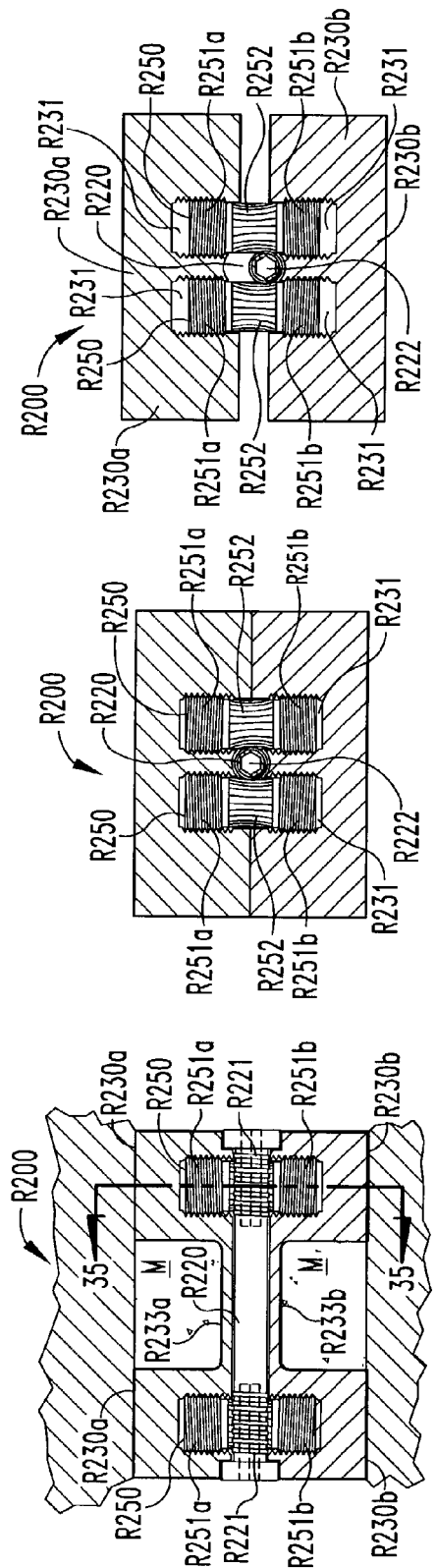
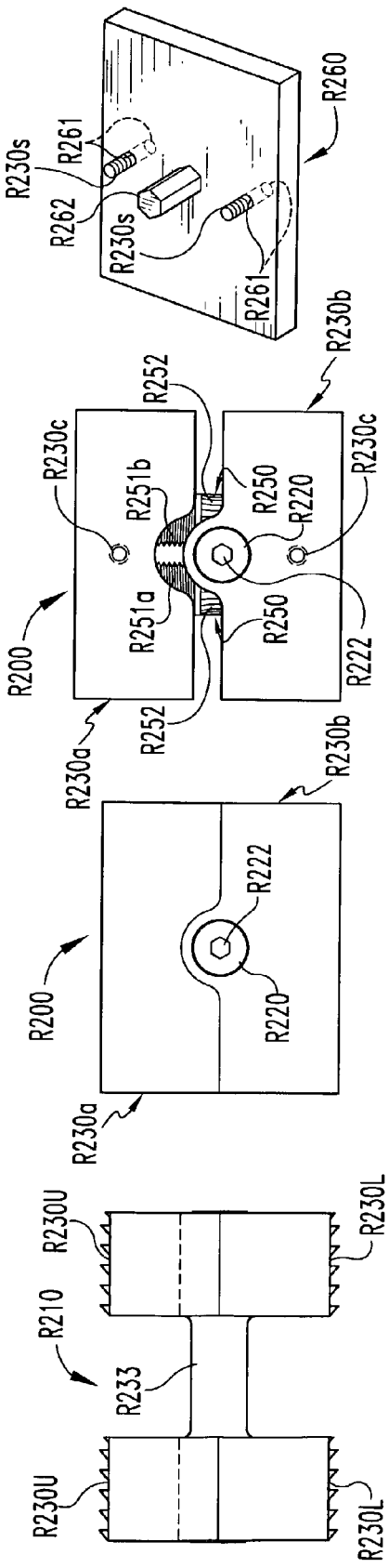

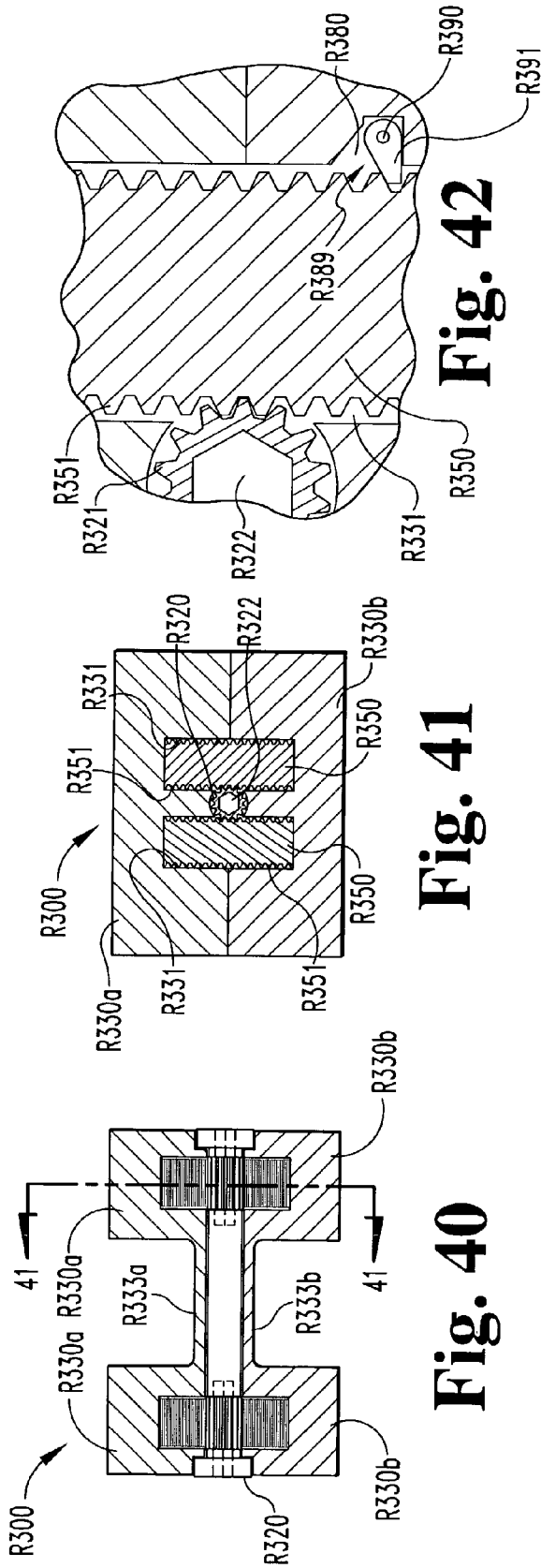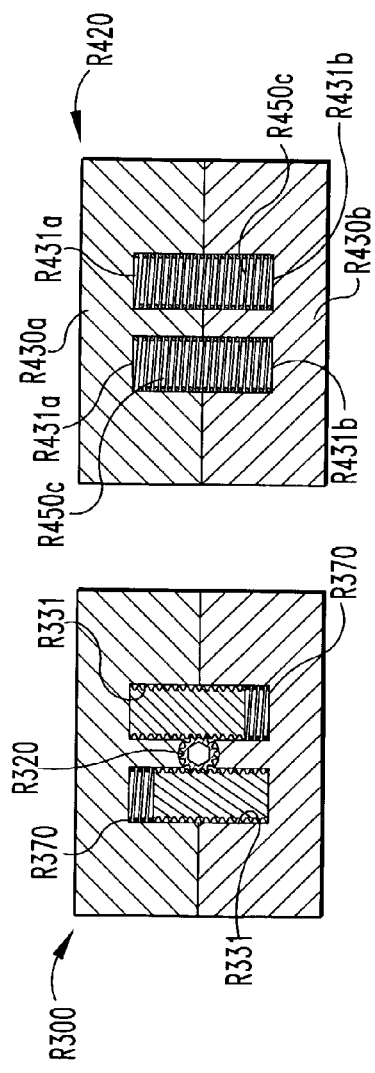

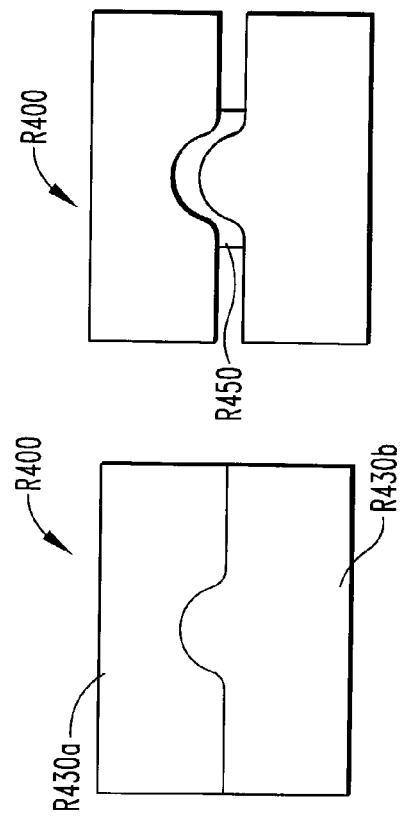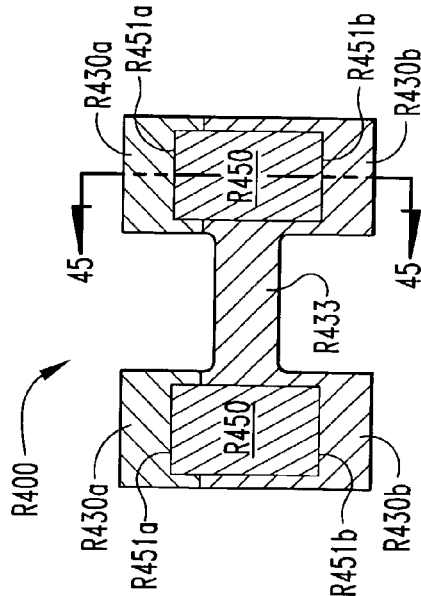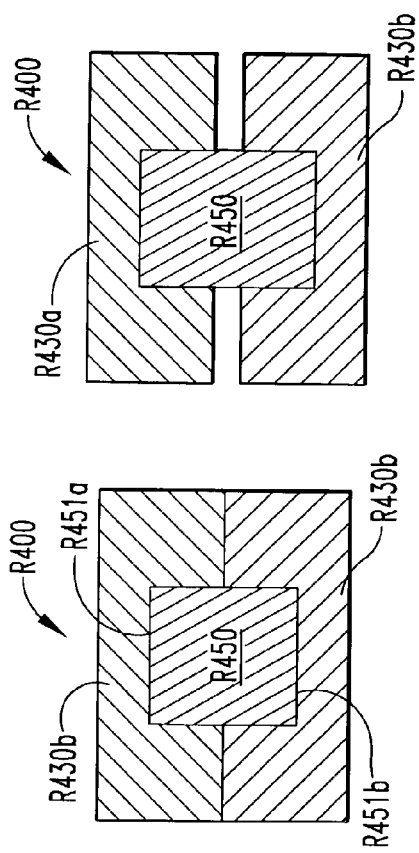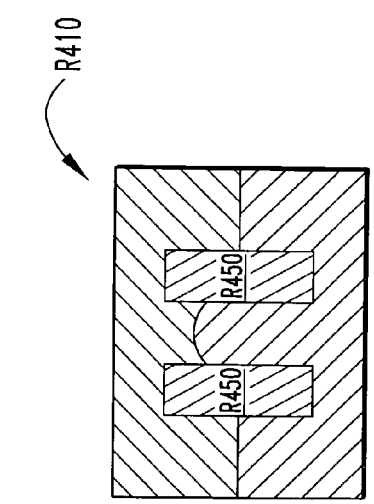

EXPANDABLE SPINAL FUSION DEVICE AND METHODS OF PROMOTING SPINAL FUSION

BACKGROUND OF THE INVENTION

The present invention relates to an implant device to be placed into a portion of the intervertebral space between adjacent vertebrae. Specifically, the invention concerns an expandable osteogenic fusion device that may enhance arthrodesis or fusion between adjacent vertebral bodies while also maintaining the height of the intervertebral space at the instrumented vertebral level.

In many cases, low back pain originates from damages or defects in a spinal disc between adjacent vertebral bodies. The disc can be herniated or can be affected by a variety of degenerative conditions. Frequently, pathologies affecting the spinal disc can disrupt the normal anatomical function of the disc. In some cases, this disruption is significant enough that surgical intervention is indicated.

In one such surgical treatment, the affected disc is essentially removed and the adjacent vertebral bodies are fused together. In this treatment, a discectomy procedure is conducted to remove the disc nucleus while retaining the annulus. Since the disc material has been removed, an implant must be placed within the intervertebral space to prevent the space from collapsing.

In early spinal fusion techniques, bone material, or bone osteogenic fusion devices, were simply disposed between adjacent vertebral bodies, typically at the posterior aspect of the vertebral bodies. In the early history of these bone osteogenic fusion devices, the devices were formed of cortical-cancellous bone which was generally not strong enough to support the weight of the spinal column at the instrumented level. Consequently, the spine was stabilized by way of a plate or a rod spanning the affected vertebral bodies. With this technique, once fusion occurred across the vertebral bodies and incorporated the bone osteogenic fusion device, the hardware used to maintain the stability of the spine became superfluous.

Following the successes of the early fusion techniques, focus was directed to modifying the device placed within the intervertebral space. Attention was then turned to implants, or interbody fusion devices, that could be interposed between the adjacent vertebral bodies, maintain the stability of the disc interspace, and still permit bone fusion or arthrodesis. These interbody fusion devices have taken many forms. For example, one prevalent form is a cylindrical hollow implant or "cage". The outer wall of the cage creates an interior space within the cylindrical implant that is filled with, for example, bone chips or other bone growth-inducing material. In recent years compounds known as bone morphogenetic proteins (BMPs) have become the preferred bone growth inducing material. In some cases, the cylindrical implants included a threaded exterior to permit threaded insertion into a tapped bore formed in portions of the adjacent vertebral bodies. Alternatively, some fusion implants have been designed to be impacted into the intervertebral space. Yet another class of fusion implants can be placed in between adjacent vertebral bodies and then expanded to contact the opposing surfaces of the vertebral bodies.

Experience with some interbody fusion devices has demonstrated the efficacy of some such implants in yielding a solid bone fusion. Variations in the design of the implants have accounted for improvements in stabilizing the motion segment while fusion occurs. Nevertheless, with some of the interbody fusion devices, there remains difficulty in achieving a complete fusion, at least without the aid of some additional stabilizing device, such as a rod or plate. Moreover, some of the devices are not structurally strong enough to support some loads and bending moments applied at certain levels of the spine.

Further difficulty has been encountered when a surgeon, desiring to avoid removal of the spinal facet joints laterally, uses an undersized interbody fusion cage in a posterior lumbar interbody fusion procedure (PLIF). Use of undersized devices results in sub-optimal contact with the endplates of adjacent vertebral bodies and consequent sub-optimal bone formation inside the device, and can lead to pseudoarthrosis. Additionally, undersized devices may not provide adequate disc space distraction and nerve root decompression. Due to the high degree of anatomical and physiological variation encountered in all surgery, efforts to avoid utilization of a posteriorly undersized implant can require the availability of numerous devices of different dimensions, and increase the time required to carry out the surgical procedure, thus increasing the cost and risk associated with the procedure. Some prior efforts to address this difficulty through use of expandable devices have utilized designs involving numerous parts, or designs that apply excessive stress force to the device, resulting in device strain. These design approaches increase the risk of mechanical failure. Also, they may occlude the space between vertebral body endplates, inhibiting fusion from adequately occurring.

Even with devices that do not have the aforementioned difficulties, still other undesirable characteristics exist. Studies have suggested that the interbody fusion implant devices, especially those implants of the "cage" design, lead to stress-shielding of bone material within the cage. It is well known that bone growth is enhanced by stressing or loading the bone material. The stress-shielding phenomenon relieves some or all of the load applied to the bone material to be fused, which can greatly increase the time for complete bone fusion, or disturb the quality and density of the ultimately formed fusion mass. In some instances, stress-shielding can cause the bone chips or fusion mass contained within the fusion cage to resorb or evolve into fibrous tissue rather than into a bony fusion mass. A further difficulty encountered with many fusion implants is that the material of the implant is not radiolucent. Most fusion cages are formed of metal, such as stainless steel, titanium or porous tantalum. The metal of the cage shows up prominently in any radiograph (x-ray) or computer tomography (CT) scan. Since "cage" type fusion devices surround and contain the bone graft material housed within a metal cage, the developing fusion mass within the cage cannot be seen under traditional radiographic visualizing techniques, and can be seen in CT scans only with the assistance of image scatter techniques. Thus, the spinal surgeon does not have adequate means to determine the progress of the fusion, and in some cases cannot ascertain whether the fusion was complete and successful.

Thus, the field of spinal fusion lacks a suitable intervertebral fusion device that can be made small enough to facilitate insertion in the intervertebral space and support bone growth material within the intervertebral space and expand to maintain the normal height of the disc space. Further, current spinal fusion devices do not sufficiently reduce the risk of stress-shielding the fusion mass and do not enable visualization of the fusion mass as the arthrodesis progresses. So, there remains a need for improvements in osteogenic fusion device technology, particularly devices that provide expandable characteristics. The present invention addresses this need in a novel and non-obvious fashion.

SUMMARY OF THE INVENTION

To address the current needs with respect to interbody fusion devices, the present invention contemplates an expandable osteogenic fusion device for promoting osteogenic fusion in an intervertebral disc space between adjacent vertebral bodies. The device includes a first configuration to enable placement with minimal surgical exposure for access to the space and a second configuration that expands in the space to provide proper disc space distraction. Further, the expanded device enables retention of an optimum amount of bone growth fusion material and placement of the bone growth inducing material into contact with adjacent bone.

In one embodiment, the expandable implant includes a cam. The cam is in contact with an interior surface of a first member. The first member contacts a portion of one of the adjacent vertebral bodies. The cam is also in contact with an interior surface of a second member. The second member contacts a portion of the other of the adjacent vertebral bodies. The implant can be expanded by simply turning the cam, and thereby without the cam undergoing substantial translational displacement, to cause one of the first member and the second member to move slightly away from the other for the desired expansion.

Another embodiment of the present invention also contemplates an expandable implant for promoting osteogenic fusion in an intervertebral disc space between adjacent vertebral bodies. This embodiment includes a first member for contacting a portion of one of the adjacent vertebral bodies and a second member for contacting a portion of the other of the adjacent vertebral bodies. The first member has a bore defined therein. The bore is threaded along substantially its entire length. This embodiment further includes a screw having a threaded region and further having a region of gear teeth. The threaded region of the screw is at least partially threaded into the bore. The screw contacts the second member in a manner permitting the screw to rotate. This embodiment further includes an axle having a threaded region. The threaded region of the axle engages the gear teeth of the screw to function as a worm and pinion gear assembly operable to produce the desired expansion.

Yet another embodiment of the present invention contemplates an expandable implant for promoting osteogenic fusion in an intervertebral disc space between adjacent vertebral bodies. This embodiment includes a first member for contacting one of the adjacent vertebral bodies and a second member for contacting the other of the adjacent vertebral bodies. This embodiment further includes a rack having a plurality of gear teeth. The rack is in contact with one of the first member and the second member. An axle having a pinion gear is further included. The axle is coupled to the other of the first member and the second member in a manner that allows the axle to rotate. The pinion gear of the axle contacts at least one of the plurality of gear teeth of the rack to form a rack and pinion operable for the expansion.

Still another embodiment of the present invention contemplates an expandable implant for promoting osteogenic fusion in an intervertebral disc space between adjacent vertebral bodies, and includes first and second initially abutting each other. The first member is substantially adjacent to one of the vertebral bodies. The second member is substantially adjacent to the other vertebral body. A spring for expanding the implant from a first configuration to a second configuration is also included in this embodiment. The spring is compressed when the implant is in the first configuration. One portion of the spring is in physical contact with the first member and another portion of the spring is in physical contact with the second member.

In still another embodiment of the present invention an expandable implant for promoting osteogenic fusion in an intervertebral disc space between adjacent vertebral bodies includes first and second initially abutting each other. The first member is substantially adjacent to one of the vertebral bodies. The second member is substantially adjacent to the other vertebral body. A manufactured body for expanding the implant from a first configuration to a second configuration is also included. The manufactured body is capable of assuming a first state and a second state. A first portion of the manufactured body is in physical contact with the first member and a second portion of the manufactured body is in physical contact with the second member to spread the first and second after insertion into the intervertebral space.

An additional set of embodiments much like those summarized above is provided with a rectangular external cross-sectional shape instead of the circular external cross-sectional shape.

An additional embodiment of the present invention contemplates a method of promoting osteogenic fusion of adjacent vertebral bodies. The method includes the step of providing an expandable implant that defines a void intermediate a part of the implant and one of the vertebral bodies when the implant is substantially adjacent to the vertebral body. The step of positioning the expandable implant substantially intermediate a first vertebral body and a second vertebral body is further included in the present embodiment of the invention. Still further included is the step of expanding the implant while maintaining the void.

In the various embodiments of the present invention, the expandable implant maintains intervertebral disc space between adjacent vertebral bodies while providing a void intermediate the vertebral bodies where the bone growth inducing material may be packed, thereby minimizing the above-mentioned stress-shielding of bone material while enabling radiographic visualization of the developing fusion mass.

Therefore, embodiments of the present invention provide an improved expandable osteogenic fusion device. Numerous advantages and additional aspects of the present invention will be apparent from the description of the preferred embodiments and drawings that follow.

BRIEF DESCRIPTION OF THE DRAWINGS

FIG. 1 is a side sectional view of a first embodiment of the present invention at line 1—1 in FIG. 2 and viewed in the direction of the arrows.

FIG. 2 is an end sectional view of the embodiment of FIG. 1 taken along line 2—2 in FIG. 1 and showing the implant in a non-expanded position.

FIG. 3 is an end view of the embodiment of FIG. 1 showing the implant in a non-expanded position.

FIG. 4 is an end sectional view of the embodiment of FIG. 1 taken along line 2—2 in FIG. 1 and showing the implant in an expanded position.

FIG. 5 is an end view of the embodiment of FIG. 1 showing the implant in an expanded position.

FIG. 6 is a view along the longitudinal axis of the embodiment of FIG. 1 taken at line 6—6 showing the implant in an non-expanded position.

FIG. 7 is a view like FIG. 6 but showing the implant in an expanded position.

FIG. 8 is a side partial sectional view of a second embodiment of the present invention.

FIG. 9 is a side view of the second embodiment of the present invention.

FIG. 10 is an end partial sectional view of the embodiment of FIG. 8 taken along line 10—10 showing the implant in a non-expanded position.

FIG. 11 is an end partial sectional view of the embodiment of FIG. 8, similar to FIG. 10, showing the implant in an expanded position.

FIG. 12 is an end view of the embodiment of FIG. 8 showing the implant in a non-expanded position.

FIG. 13 is end view of the second embodiment of the present invention showing the implant in an expanded position.

FIG. 14 is a perspective view of a locking cap.

FIG. 15 is a side partial sectional view of a third embodiment of the present invention.

FIG. 16 is an end sectional view of the embodiment of FIG. 15 taken along line 16—16 showing the implant in an non-expanded position.

FIG. 17 is a detailed view of a portion of the third embodiment showing a ratcheting mechanism.

FIG. 18 is an end sectional view of a variation similar to FIG. 16, showing the implant in an non-expanded position and including springs.

FIG. 19 is an end sectional view of a variation showing an implant in non-expanded position with only springs.

FIG. 20 is an end sectional view of a second variation of a fourth embodiment of the present invention taken along line 20—20 of FIG. 24 showing the implant in a non-expanded position.

FIG. 21 is an end sectional view of the second variation of the fourth embodiment of the present invention showing the implant in an expanded position.

FIG. 22 is an end view of the second variation of the fourth embodiment of the present invention showing the implant in a non-expanded position.

FIG. 23 is an end view of the second variation of the fourth embodiment of the present invention showing the implant in an expanded position.

FIG. 24 is a side sectional view of the second variation of the fourth embodiment of the present invention showing the implant in a non-expanded position.

FIG. 25 is an end sectional view of a third variation of the fourth embodiment of the present invention showing the implant in a non-expanded position.

FIGS. 26 through 50 illustrate various embodiments generally corresponding to those shown in FIGS. 1 through 25 but wherein the configuration of the implants as viewed along the implant axis is generally rectangular, rather than circular.

DESCRIPTION OF THE ILLUSTRATED EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Such alterations and further modifications in the illustrated device and such further applications of the principles of the invention as illustrated therein as would normally occur to one skilled in the art to which the invention relates are contemplated as within the scope of the invention.

The drawings show various embodiments of an implant for insertion into the intervertebral space between adjacent vertebrae and include first and second end members for engaging respective ones of the adjacent vertebrae, and an expansion member for changing the implant from a first state suitable for insertion into the intervertebral space between the distracted vertebrae, to a second state suitable for maintaining a predetermined spacing between the adjacent vertebrae. The expansion member may include any system or mechanism for changing the spacing between upper and lower portions of the first end member and upper and lower portions of the second end member in a direction substantially aligned with the longitudinal axis of the spine at the site of the adjacent vertebra, while maintaining substantially the same position in an axis perpendicular to the longitudinal axis of the spine. Additionally, the first and second end members have lateral portions that are spaced apart and define an intermediate chamber between the adjacent vertebrae suitable for retaining a bone growth-inducing material. The expanded end members can handle loads imposed while maintaining the predetermined spacing during fusion. By communicating with the adjacent vertebrae, the intermediate chamber allows the transmission of loads from one vertebrae to the adjacent vertebrae through the bone growth inducing material, thereby facilitating fusion. Thus, the implant maintains the predetermined spacing between the adjacent vertebrae while promoting fusion of the adjacent vertebrae through the bone growth inducing material.

In accordance with a first embodiment of the present invention, an expandable osteogenic fusion implant 8, depicted in FIGS. 1–7, has a cam-action expansion member. Implant 8 includes cams 10 connected at opposite ends of a connecting member 20, and two end members 30, respectively, enclosing each cam. Cams 10 have an outer surface that contacts a first portion of the inner surface of each of the ends 10 when the implant is not expanded, but when rotated as in FIG. 4, the cams 10 contact a second portion of each of the end members 30. The end members 30 further include exterior surfaces 32 that contact the endplates of the vertebral bodies 21 and 22, respectively, above and below the disc space "S" of FIG. 1 when the implant is in an expanded configuration. Exterior surfaces 32 may include a bone engaging configuration 65, such as threads or ridges to promote a secure positioning of the implant or to enable insertion of the implant. The implant transforms from the non-expanded configuration to the expanded configuration by, for example, a rotation of the cams 10 about the longitudinal axis of connecting member 20. As the cams 10 rotate, they exert forces on surfaces 31 of end members 30 that cause end members 30 to move apart from one another. By selecting the size and configuration of the cooperating surfaces of the cams 10 and end members 30, the expansion of the implant can be controlled to provide desired distraction of adjacent vertebral bodies and nerve root decompression. Expansion distances of one to eight millimeters, depending on the size and shape of the implant, such as one to three for small, one to six for medium, and one to eight for large, are examples. It will be appreciated by one of ordinary skill in the art that cams 10, while illustrated as largely identical in FIG. 1, may have different shapes, sizes and configurations from one another. Similarly, one of ordinary skill in the art will recognize that end members 30 while illustrated as substantially identical in FIG. 1, may also have different shapes, sizes and configurations from one another.

In this embodiment, the cams 10 are positioned and secured at opposite ends of the elongate connecting member 20 that extends intermediate the cams 10. Member 20 and cams 10 may be one integral homogeneous piece of material, or may be separate pieces joined together. Some examples of techniques for connecting member 20 and cams 10 include staking, threading, screwing, bolting, or welding. Additionally, connecting member 20 may be configured to join cams to along their axes of rotation, or may be configured to connect the cams at any position that transmits the rotation of one cam to the other cam. Additionally, one or more cams 10 may be positioned at any point along central member 20.

Variations of the embodiment described above and shown in FIGS. 1–7 are within the scope of the invention. For example, one of cams 10 is shown in FIGS. 2 and 4 as having a substantially elliptical cross sectional shape, however, it is contemplated that cams 10 could have almost any cross sectional shape that would provide a greater distance along a first axis than along a second axis while permitting the cam to be intentionally turned by the surgeon. For instance, cams 10 could have an oval cross section or a cross section that is generally rectangular with rounded corners. It should be understood also that interior surfaces 31 can also assume a variety of shapes cooperating with the shape of the cams 10. Regardless of the specific cross sectional shape of the cams 10 and the shape of interior surfaces 31, implant 8 may include a retainer mechanism to secure the position of cams 10 and thereby maintain the implant in the expanded position. For example, interior surfaces 31 may be adapted to hold cams 10 in a fixed position when the implant has been transformed to the expanded position. Referring to FIGS. 2 and 4, for example, retainer mechanism includes cavities 33 formed along interior surfaces 31 that are not occupied in the non-expanded position (see FIG. 2), but that are occupied by the cams 10 in the expanded position (see FIG. 4). For example, cavities 33 include surfaces having a radius of curvature less than the radius of curvature of the corresponding portion of the surface of the cam. As such, a predetermined difference in the radius of curvatures requires a predetermined rotational force to move the cam out of the cavity. In other embodiments, the retainer mechanism may include notches, tabs and other similar structures to secure the cams to hold the implant in the expanded position. Thus, in the expanded position, the portions of interior surfaces 31 that define the cavities 33 in the non-expanded position contact the cams 10 and resist movement of the cams 10 out of the expanded position.

It will further be understood that exterior surfaces 32, while in one embodiment may be substantially semi-circular in shape, as shown in FIGS. 2–7, can be provided in a variety of other shapes. Moreover, it is contemplated that at least portions of surfaces 32 may also include a variety of adaptations designed to secure them to the surface of a vertebral body. The surfaces 32 may include bumps, ridges, threads, spikes, grooves, slots or other features to ensure that the surfaces 32 securely contact the vertebral body and do not slip out of position.

Additionally, each of end members 30 may include a truncated outer wall 30T (FIG. 1). Truncated wall 30T defines an access gap 38 that provides access to one of the cams 10 from the exterior of implant 8. Cam 10 may further include a tool receptacle 21, shown in FIGS. 3 and 5. Tool receptacle 21 can be provided in a wide variety of shapes, including but not limited to a Phillips head shape, a flathead shape, a star shape, a hex-wrench shape, and a square shape. The receptacle 21 facilitates the expansion of the implant by receiving a tool (not shown) that may be turned to cause the rotation of the cams 10.

Additionally, implant 8 may further include an assembly connector device or mechanism to hold end members 30 together with the cams 10 and thus prevent the components of the implant from becoming completely separated during handling and insertion into the intervertebral space. The assembly connector may include any structure that maintains a connection between the end members 30 and the cams 10. One example is a fine wire encircling the ends and which may be permanent or biodegradable or absorbable. If permanent, it would not be strong enough to resist the expansion feature of the invention. In another connector example shown in FIGS. 6–7, implant 8 includes pins 14 projecting through slots 37 in a wall 30C of each of the respective top and bottom end members 30. The pins are fixed in shoulders 10T of each of the cams 10. The slots 37 receive the pins 14 and the pins thus retain the end members 30 about the cams 10. The slots 37 are configured to form a path defined by the pins 14 as the cams 10 rotate. If desired, an assembly connector device or mechanism may take the form of any shaped protrusion and corresponding slot, or any other device or mechanism that prevents the cams 10 and end members 30 from becoming completely separated during insertion or during handling prior to insertion of the implant.

Additionally, referring to FIG. 1, implant 8 includes internal chamber ends 60, defined by walls 30c of end members 30, elongate connecting member 20, and by adjacent vertebral bodies 21 and 22 when the implant is inserted between the adjacent vertebral bodies. Chamber 60 may be filled with a material that promotes bone growth. A variety of such bone growth promoting materials may be used. For example, chamber 60 may be packed with a material composition including an osteoinductive factor such as bone morphogenetic protein (BMP) or LIM mineralization protein (LMP). For example, BPM-1, BMP-2 or BMP-11 might be used. Demineralized bone matrix (DBM), bone in particulate form such as chips or powder, might also be used. A conductive or scaffolding material might also be used. Examples are bone, or a bioceramic such as biocompatible calcium phosphate ceramics. Examples of those include biphasic calcium phospate, tricalcium phosphate, and preferably a hydroxyapatite paste material such as described in ETEX, Corp. U.S. Pat. Nos. 6,331,312, 6,214,368, 6,117, 456, and 6,027,742. Numerous methods could be used to fill chamber 60. For example a paste could be packed within chamber 60. Another alternative is to spool a collagen sheet coated with BMP around the connecting member 20. The sheet may have a width substantially equivalent to the width of chamber 60 defined by end members 30. Yet another possibility is to inject bone growth promoting material through the gaps 61 (FIG. 5) when the implant is in an expanded position. Also, if two implants according to this embodiment are positioned side-by-side within disc space "S", then space is provided for inserting bone growth promoting materials in chamber 60.

In accordance with a second embodiment of the present invention, shown in FIGS. 8–14, an expandable osteogenic fusion implant 200 includes a screw-type expansion member. Implant 200 includes end members with upper end portions 230a and lower end portions 230b, each having one or more threaded bores 231 (FIG. 11). In one version of this second embodiment, shown in FIG. 8, elongate central members 233a and 233b extend between and connect the upper end portions 230a and the lower end portions 230b, respectively, of the end members. Alternatively, in another embodiment, and referring to FIG. 9, implant 210 includes only one elongate central member 233 extending between either the upper end portions 230U or the lower end portions 230L. In either case, the elongate central members 230a, b, or member 233, if only one is to be used, may be attached to the upper or lower end portions. Some examples of suitable attachment methods are welding, screwing or bolting. Alternatively, end portions 230a and 230b and the elongate central member portions 233a, b and member 233 may be manufactured as one piece. The implant 200 further includes screws 250, each having screw threads 251a and 251b and gear teeth 252 (FIGS. 10, 11 and 13). Referring to FIGS. 8 and 10, there are four of these screws although more or fewer screws may be utilized. The implant 200 also includes central axle 220 having central axle threads 221 at each end (FIG. 8) which act as a gear worm engaging the gear teeth 252 to turn the screws and expand the implant.

Screw threads 251a at one end of screws 250 are left hand threaded, and screw threads 251b at the other end of screws 250 are right hand threaded. Thus rotating a screw 250 about its longitudinal axis in a first direction will cause the screw 250 to thread itself into threaded bore 231 of upper end member 230a and into threaded bore 231 of lower end member 230b. Rotating a screw 250 in a second direction opposite the first will cause screw 250 to thread itself out of threaded bore 231 of upper end member 230a and thread itself out of threaded bore 231 of lower end member 230b. Alternately, each screw and bore may only be threaded at one end. In another embodiment, the upper and lower end portions are not connected by a central portion, and the screws and bores at opposite ends of the implant have differently pitched threads, thereby expanding each end at a different rate to impart a predetermined curvature to the adjacent vertebrae.

Central axle 220 is positioned between upper end 230a and lower end 230b. Central axle 220 is further positioned so that central axle threads 221 contact gear teeth 252 of each of the screws 250. This configuration forms a plurality of worm gears. When central axle 220 is rotated about its longitudinal axis, central axle threads 221 successively engage gear teeth 252 of the screws 250 thus causing the screws 250 to rotate about their longitudinal axes. Due to the fact that the screws 250 on each end of implant 200 are positioned on opposite sides of the central axle 220, turning the central axle 220 will cause the screws 250 to turn in opposite directions as the central axle threads 221 engage the gear teeth 252. Thus, the rotation of central axle 220 causes the expansion of the implant by rotating the screws 250.

It should be understood that screws 250 might include only one of threaded portions 251a and 251b. In such case, a smooth shank portion (not shown) may be substituted for the omitted one of threaded portions 251a and 251b. Also, one of the upper end 230a and lower end 230b may have bores 231 that are unthreaded and that receive the smooth shank portions. While rotation of the screws will cause displacement of the end in which they are threaded, such as upper end 230a, the smooth shank portions of the screws will rotate freely in the unthreaded bores, such as in lower end 230b, and that end will not be displaced. The resulting expansion of implant 200 is shown in FIG. 13.

Additionally, implant 200 may include tool receptacle 222 at one end of central axle 200 for receiving a tool to rotate the central axle and expand or contract the implant. Tool receptacle 222 may have a variety of shapes including but not limited to a hexagonal wrench shape, a star shape, a Phillips head shape, a flathead shape, and a square shape. The implant 200 may further include locking cap 260 (FIG. 14) that connects to the end of the implant having tool receptacle 222 to prevent rotation of central axle 222. In one embodiment, locking cap 260 has an inside face 260a having a post 262 adapted to fit into turning tool receptacle 222. Locking cap 260 further includes screw holes 261 to receive screws 230s inserted from the outside face and screwed into screw holes 230c and 230d after the desired expansion has been established. Thus, locking cap 260 is capable of preventing central axle 220 from rotating about its longitudinal axis by engaging post 262 with turning tool receptacle 222 and by further engaging the engaging screws with upper end member 230a and lower end member 230b by passing them through screw holes 261 and threading them into upper end member 230a and lower end member 230b. Other devices, such as pins, rivets or posts could be substituted for screws.

In operation, since the central axle 220 drives screws 250 on opposite sides (i.e. the left and right sides as viewed in FIGS. 10 and 11) of central axle 220, the screws are threaded into threaded bores 231 of common upper end member 230a in opposite directions. Thus the screws 250 on opposite sides of the central axle 220 would turn in opposite directions. So when axle 220 is rotated, the screws are simultaneously either threading into or out of the bores 231, depending on the direction of shaft rotation. So they simultaneously move the member 230a in the same direction relative to the screws. As stated above, the threads on opposite ends of each screw may be oppositely threaded. So screws 250 are threaded into threaded bores 231 of the common lower end member 230b in the direction opposite that in the common upper end member. Thus both ends of the screws 250 accomplish the same movement relative to the upper and lower end, either threading into or out of the bores 231.

In accordance with a third embodiment, referring to FIGS. 15–18, an expandable osteogenic fusion implant 300 includes a rack-and-pinion type expansion member. implant 300 includes upper end 330a and lower end 330b, having corresponding bores 331. Elongate central portions 333a and 333b extend between and connect the respective upper end portions 330a and the lower end portions 330b. Alternatively, only one elongate central member 333 may be included extending between either the upper end portions 330a or the lower end portions 330b. In either case, the elongate central member may be permanently or removably attached to the end portions 330a and/or 330b, such as by welding, screwing or bolting. Alternatively, the end portions 330a and 330b and the elongate member 333 may be formed as one piece. The implant 300 further includes gear racks 350, having rack teeth 351, disposed within each bore 331. The implant 300 also includes central axle 320 having central axle gear teeth 321 corresponding with rack teeth 351. Gear teeth 321 may be disposed directly on central axle 320 or, alternatively, may be disposed on a separate pinion gear that is adapted to fit around the axle.

In operation, rack teeth 351 of one rack 350 contact the gear teeth 321 on one side of the central axle 320. Rack teeth 351 of another rack 350 contact the gear teeth 321 on the other side of the central axle 320. This configuration forms a plurality of racks and pinions. Central axle 320 is positioned intermediate upper end 330a and lower end 330b. When central axle 320 is rotated about its longitudinal axis, central gear teeth 321 successively engage teeth 351 of the racks 350 thus cause the racks 350 to be displaced. Due to the fact that the racks 350 are positioned on opposite sides of the central axle 320, rotation of the central axle 320 will cause the racks 350 to be displaced in opposite directions when the gear teeth 321 engage the respective rack teeth 351. Thus when adjacent racks 350 are displaced, one of them will come into contact with the end of bore 331 in upper end member 330a and the other will come into contact with the end of bore 331 in lower end member 330b. When the racks contact bore ends in 330a and 330b, they will exert forces upon them. The force exerted upon the upper end member 330a will be in a first direction and the force exerted upon the lower end member 330b will be in a second opposite direction. Due to the opposing nature of these forces, rotating central axle 320 will cause the expansion of the implant 300. In another embodiment similar to implant 300, referring to FIG. 18, an implant 300 may further include springs 370, disposed in bores 331. Springs 370 contact racks 350 and bores 331 and exert a force upon racks 350 to assist in the expansion of the implant. Springs could be added to implants 200 and 210 (FIGS. 8–13), if desired.

Further, referring to FIG. 16, central axle 320 includes a tool receptacle 322 at one end. Tool socket 322 may be provided in a variety of shapes including, but not limited to a hexagonal wrench shape, a star shape, a Phillips head shape, a flathead shape, and a square shape. Rotation of the central axle 320 may be accomplished by inserting the tool into the tool receptacle 322 and rotating the tool. A T-handled Allen wrench is one example of a tool. The implant may further include a locking cap 260, as shown in FIG. 14 and functioning as described above, including a post 262 adapted to fit into turning tool receptacle 322.

Additionally, implant 300 may include ratcheting mechanisms 389 (FIG. 17) disposed in recess 380 formed in bores 331 of upper end 330a and lower end 330b. Suitable ratcheting mechanisms 389 include, for example, axles 390 and engaging bodies 391. Recesses 380 allow the engaging bodies 391 to pivot in a first direction, but to prevent pivoting past a certain position in a second opposite direction. Engaging bodies 391 are shaped to fit between and engage the rack teeth 351 (FIG. 17). When racks 350 are displaced in a first direction, rack teeth 351 exert a force on engaging bodies 391 and cause them to pivot in a first direction and move partially into recesses 380, and then the bodies pivot back into the next successive space between the teeth as the rack is further displaced. In their original position, the bodies 391 contact one side of recesses 380, thereby preventing pivoting of the bodies in that direction. When engaging bodies 391 can no longer pivot and are positioned intermediate the rack teeth 351, the rack 350 is prevented from moving further in the second direction. In this manner, the implant may be ratcheted open. Additionally, a biasing member such as a spring may be used to force the body in the non-pivoting position. Other ratcheting mechanisms could be substituted for ratcheting mechanisms 389. For example, mechanisms that do not pivot, but flex, could be used.

In another embodiment of the invention, variations include biasing-type expansion members. Referring specifically to FIGS. 20–24, implant 400 includes upper and lower end 430a and 430b having cavities 451a and 451b. Elongate central member 433 extends between lower ends 430b. Alternatively, elongate central member 433 may extend between the upper ends 430a. In another alternative, an upper and a lower elongate central member may extend, respectively, between the upper end member 430a and the lower end member 430b. In any case, the elongate central member 433 may be fixably or removably attached to the end 430a and/or 430b, such as welding, screwing or bolting. Alternatively, the end and the elongate member may be formed as one piece.

The expandable osteogenic fusion implant 400 further includes bodies 450 having upper surfaces 451a and lower surfaces 451b abutting the ends of the bores in each end 430a and 430b. The bodies 450 are made of a material that is capable of assuming multiple shapes. One of ordinary skill in the art will appreciate that a wide variety of materials and structures may be used to construct bodies 450. For example, bodies 450 may be made of a shape memory alloy. In this case the bodies 450 could be designed to change shape or, alternatively, to expand when subjected to specific environmental conditions, such as heating or cooling the implant. The implant 400 of FIGS. 20–24 have a single body in each end member, while FIG. 25 shows how two bodies could be used in an end member. Phase change expansion of a few millimeters may be achieved.

Bodies 450 may be compressible bodies. Some examples are a polymer or other elastomer or a spring. Suitable examples of a spring includes coil springs, leaf springs, springs made of shape memory alloy and any other spring-like member. In these cases, an external force applied to the bodies (as by a tool) causes the bodies 450 to assume a compressed state, and the bodies 450 could then be held in that state until the implant is inserted into the desired surgical position. At that time the force compressing the bodies 450 could be released or reduced and the bodies could reassume a relaxed state, thereby expanding the implant by a predetermined amount. The variation 420 shown in FIG. 19 is an example using coil springs 450c as the compressible body.

In the FIG. 25 variation, implant 410 may include multiple bodies 450 of either a phase change type of material or a compressible body disposed within the ends 410a and 410b to cause expansion of the implant.

It is of note that, when viewed along their longitudinal axes, the implants described above are circular. Their ends have a short cylindrical shape.

Referring now to FIGS. 26–50, the reference numerals used for implant components having functions similar to or identical to those described above with reference to FIGS. 1–25, are as used in FIGS. 1–25 but with the letter R in front of them. These implants, when viewed along their longitudinal axes, are rectangular. Their ends have the shape of a short parallelepiped.

A set of barbs 510 is provided on each of the end members R30 so that, after pushing or impacting the implant in the direction of arrow 520 into the intervertebral space, there will be added resistance to movement in the opposite direction out of the space. These barbs can be provided on the top surface and bottom surface such as shown at the top and bottom in FIGS. 26, 27, 29, 31, and 32, extending entirely across the implant. They can also be provided in other shapes, numbers and in multiples across one row with various spacings, as desired. They are not shown in FIGS. 28 and 30 in order to avoid congestion in the illustration where the intent is to show, in FIG. 28, slight spacing between the vertebral endplates and the top and bottom of the end members R30, and to show in FIG. 30 the closure of the space between the end members and the vertebral plates as the implant has been expanded. Barbs are also shown on the top and bottom faces of the end members of variation R210 in FIG. 34. As indicated above, barbs can be omitted from one or both end members of these and the other embodiments, if desired. This can be observed in FIGS. 33, 35–38, 40, 41, and 43–50, for example.

In the various embodiments of FIGS. 1–25, the end can be externally screw threaded as shown at 65 for example in FIG. 1, so that they can be screwed into the intervertebral disc space, if desired. Even without threads, they can be simply pushed or impacted into the space. The embodiments of FIGS. 26–50 can be pushed or impacted into the space regardless of whether they are provided without barbs or with barbs such as shown in FIG. 26 for additional anchorage. But due to the fact that the implants are expandable, they can be made small enough that they can be inserted into the intervertebral space without impacting them and then they can be expanded to maintain the desired spacing of the plates of the adjacent vertebral bodies, according to the present invention.

While the invention has been illustrated and described in detail in the drawings and foregoing description, the same is to be considered as illustrative and not restrictive in character, it being understood that all changes and modifications to the described embodiments that come within the spirit of the invention are desired to be protected.

What is claimed is:

1. A spinal implant positionable in an intervertebral disc space between adjacent vertebral bodies in a spine and comprising:
   a first cam having a substantially planar face and an extension extending along an axis substantially perpendicular to said face;
   a first member for contacting an endplate of one of the adjacent vertebral bodies, the first member having a first surface, at least a portion of the first surface being in physical contact with a portion of the first cam;
   a second member for contacting an endplate of the other of the adjacent vertebral bodies, the second member having a second surface, at least a portion of the second surface being in physical contact with a portion of the first cam,
   wherein the first cam is capable of causing one of the first member and the second member to move apart from the other of the first and second member without the first cam undergoing substantial translational displacement;
   a second cam;
   a third member for contacting the endplate of the one of the adjacent vertebral bodies, the third member having a third surface, at least a portion of the third surface being in physical contact with a portion of the second cam;
   a fourth member for contacting the endplate of the other of the adjacent vertebral bodies, the fourth member having a fourth surface, at least a portion of the fourth surface being in physical contact with a portion of the second cam; and
   an elongate member extending intermediate the first cam and the second cam, the elongate member having a first end region attached to one of the first cam and the second cam and a second end region attached to the other of the first cam and the second cam.

2. A spinal implant positionable in an intervertebral disc space between adjacent vertebral bodies in a spine and comprising:
   a first cam;
   a first member for contacting an endplate of one of the adjacent vertebral bodies, the first member having a first surface, at least a portion of the first surface being in physical contact with a portion of the first cam;
   a second member of contacting an endplate of the other of the adjacent vertebral bodies, the second member having a second surface, at least a portion of the second surface being in physical contact with a portion of the first cam; and
   wherein the first cam is capable of causing one of the first member and the second member to move apart from the other of the first and second member without the first cam undergoing substantial translational displacement; and
   a second cam;
   a third member for contacting the endplate of the one of the adjacent vertebral bodies, the third member having a third surface, at least a portion of the third surface being in physical contact with a portion of the second cam;
   a fourth member for contacting the endplate of the other of the adjacent vertebral bodies, the fourth member having a fourth surface, at least a portion of the fourth surface being in physical contact with a portion of the second cam;
   an elongate member extending intermediate the first cam and the second cam, the elongate member having a first end region attached to one of the first cam and the second cam and a second end region attached to the other of the first cam and the second cam; and;
   wherein the first member and the second member are spaced apart from the third member and the fourth member thereby defining walls for an intermediate chamber between and communicable with the endplates of both of the adjacent vertebral bodies.

3. The implant of claim 2 further comprising an osteogenic fusion promoting material disposed between said walls for engagement with the endplates of the adjacent vertebral bodies.

4. The implant of claim 3 wherein the osteogenic fusion promoting material is selected from the group consisting of BMP, LMP, and DBM.

5. A spinal implant for insertion within the disc space between adjacent vertebral bodies and comprising:
   a first end member having a first portion for engaging an endplate of one of said adjacent vertebral bodies and having a second portion for engaging an endplate of the other of said adjacent vertebral bodies, the first portion and second portion being spaced apart;
   a second end member having a third portion for engaging the endplate of one of said adjacent vertebral bodies and having a fourth portion for engaging the endplate of the other of said adjacent vertebral bodies, the third portion being spaced apart from the fourth portion; and
   means engaging said first and second end members for changing spacing between said first and second portions and for changing the spacing between said third and fourth portions, said means including a first piece engaging said first and second portions, a second piece engaging said third and fourth portions, and a third piece linking said first and second pieces.

6. The spinal implant of claim 5 and wherein the means for changing the spacing is selected from the group consisting of a cam mechanism, a screw mechanism, a rack and pinion mechanism, and a biasing mechanism.

7. The spinal implant of claim 5 and further comprising:
   an elongate member intermediate said first end member and said second end member for cooperating with faces of said first and second end members to define a chamber between the endplate of said one vertebral body and the endplate of said other vertebral body for receiving bone growth inducing material within said chamber.

8. The combination of claim 7 and further comprising:
bone growth material received between said end members and around said elongate member to fill said chamber.

9. The combination of claim 8 and wherein the bone growth inducing material is selected from a group consisting of bone, BMP, LMP, and DBM.

10. The spinal implant of claim 5 and wherein:
said first and second end members have a rectangular shape.

11. The spinal implant of claim 5 and wherein:
the first and second end members have short parallelepiped shapes.

12. The spinal implant of claim 5 and further comprising:
an elongate member connected to said end members and having a longitudinal axis; and
said end members are polygonal in spaced planes perpendicular to said longitudinal axis.

13. The spinal implant of claim 12 and wherein:
said portions for engaging said vertebral bodies have surface projections for anchoring in said vertebral bodies.

14. The spinal implant of claim 13 and wherein:
said surface projections are barbs.

15. A spinal implant positionable in an intervertebral disc space between adjacent vertebral bodies in a spine and comprising:
a first cam;
a first member for contacting an endplate of one of the adjacent vertebral bodies, the first member having a first surface, at least a portion of the first surface being in physical contact with a portion of the first cam;
a second member of contacting an endplate of the other of the adjacent vertebral bodies, the second member having a second surface, at least a portion of the second surface being in physical contact with a portion of the first cam; and
wherein the first cam is capable of causing one of the first member and the second member to move apart from the other of the first and second member without the first cam undergoing substantial translational displacement; and
an assembly connecting mechanism including a first object protruding from the first cam; and
a slot in the first member shaped to receive the first object, and
a second cam;
a third member for contacting the endplate of the one of the adjacent vertebral bodies, the third member having a third surface, at least a portion of the third surface being in physical contact with a portion of the second cam;
a fourth member for contacting the endplate of the other of the adjacent vertebral bodies, the fourth member having a fourth surface, at least a portion of the fourth surface being in physical contact with a portion of the second cam;
an elongate member extending intermediate the first cam and the second cam, the elongate member having a first end region attached to one of the first cam and the second cam and a second end region attached to the other of the first cam and the second cam.

16. The apparatus of claim 15, wherein the first member and the second member are spaced apart from the third member and the fourth member thereby defining walls for an intermediate chamber between and communicable with the endplates of both of the adjacent vertebral bodies.

17. A spinal implant positionable in an intervertebral disc space between adjacent vertebral bodies in a spine and comprising:
a first cam;
a first member for contacting an endplate of one of the adjacent vertebral bodies, the first member having a first surface, at least a portion of the first surface being in physical contact with a portion of the first cam;
a second member for contacting an endplate of the other of the adjacent vertebral bodies, the second member having a second surface, at least a portion of the second surface being in physical contact with a portion of the first cam;
a second cam;
a third member for contacting the endplate of the one of the adjacent vertebral bodies, the third member having a third surface, at least a portion of the third surface being in physical contact with a portion of the second cam;
a fourth member for contacting the endplate of the other of the adjacent vertebral bodies, the fourth member having a fourth surface, at least a portion of the fourth surface being in physical contact with a portion of the second cam;
an elongate member extending intermediate the first cam and the second cam, the elongate member having a first end region attached to one of the first cam and the second cam and a second end region attached to the other of the first cam and the second cam;
wherein at least one of said cams is capable of causing at least one of said members it contacts to move apart from the other without said cams undergoing substantial translational displacement.

* * * * *